US008697108B2

(12) United States Patent
Ringeisen et al.

(10) Patent No.: US 8,697,108 B2
(45) Date of Patent: *Apr. 15, 2014

(54) METHOD FOR MAKING A POROUS POLYMERIC MATERIAL

(75) Inventors: Timothy A. Ringeisen, Exton, PA (US); Scott M. Goldman, Downingtown, PA (US)

(73) Assignee: Kensey Nash Corporation, Exton, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/948,486

(22) Filed: Sep. 23, 2004

(65) Prior Publication Data

US 2005/0075408 A1    Apr. 7, 2005

Related U.S. Application Data

(60) Continuation-in-part of application No. 10/864,143, filed on Jun. 9, 2004, now abandoned, which is a continuation-in-part of application No. 10/856,329, filed on May 28, 2004, now abandoned, which is a continuation of application No. 10/010,304, filed on Nov. 8, 2001, now abandoned, application No. 10/948,486, which is a continuation-in-part of application No. 10/830,267, filed on Apr. 21, 2004, now Pat. No. 7,963,997, which is a continuation of application No. 10/199,961, filed on Jul. 19, 2002, now abandoned, which is a continuation-in-part of application No. 09/206,604, filed on Dec. 7, 1998, now Pat. No. 6,264,701, which is a division of application No. 08/242,557, filed on May 13, 1994, now Pat. No. 5,981,825.

(60) Provisional application No. 60/386,191, filed on Jul. 19, 2001.

(51) Int. Cl.
*A61F 2/00* (2006.01)

(52) U.S. Cl.
USPC .......................................... 424/423; 424/422

(58) Field of Classification Search
None
See application file for complete search history.

(56) References Cited

U.S. PATENT DOCUMENTS

| 3,492,154 | A | * | 1/1970 | Einstman | 427/246 |
|---|---|---|---|---|---|
| 3,527,653 | A | | 9/1970 | Sommer et al. | |
| 3,553,008 | A | * | 1/1971 | Reischl et al. | 427/246 |
| 3,619,250 | A | | 11/1971 | Nishijima | |
| 3,953,566 | A | | 4/1976 | Gore | |
| 3,974,526 | A | | 8/1976 | Dardik et al. | |
| 4,171,390 | A | | 10/1979 | Hilterhaus et al. | |
| 4,173,689 | A | | 11/1979 | Lyman et al. | |
| 4,187,390 | A | | 2/1980 | Gore | |
| 4,355,426 | A | | 10/1982 | MacGregor | |
| 4,474,630 | A | | 10/1984 | Planck et al. | |
| 4,482,516 | A | | 11/1984 | Bowman et al. | |
| 4,485,097 | A | | 11/1984 | Bell | |
| 4,520,821 | A | | 6/1985 | Schmidt et al. | |
| 4,594,407 | A | | 6/1986 | Nyilas et al. | |
| 4,605,513 | A | | 8/1986 | DiMarchi | |
| 4,657,544 | A | | 4/1987 | Pinchuk | |
| 4,673,418 | A | * | 6/1987 | Peinemann | 96/10 |
| 4,731,073 | A | | 3/1988 | Robinson | |
| 4,769,286 | A | * | 9/1988 | Le Noane | 428/372 |
| 4,955,899 | A | | 9/1990 | Della Corna et al. | |
| 5,019,096 | A | | 5/1991 | Fox, Jr. et al. | |
| 5,024,671 | A | | 6/1991 | Tu et al. | |
| 5,041,138 | A | | 8/1991 | Vacanti et al. | |
| 5,077,049 | A | * | 12/1991 | Dunn et al. | 424/426 |
| 5,128,382 | A | * | 7/1992 | Elliott et al. | 521/178 |
| 5,132,066 | A | | 7/1992 | Charlesworth et al. | |
| 5,133,755 | A | | 7/1992 | Brekke | |
| 5,163,951 | A | | 11/1992 | Pinchuk et al. | |
| 5,166,187 | A | | 11/1992 | Collombel et al. | |
| 5,229,045 | A | | 7/1993 | Soldani | |
| 5,246,452 | A | | 9/1993 | Sinnott | |
| 5,268,178 | A | | 12/1993 | Calhoun et al. | |
| 5,294,446 | A | | 3/1994 | Schlameus et al. | |
| 5,306,311 | A | | 4/1994 | Stone et al. | |
| 5,376,376 | A | | 12/1994 | Li | |

(Continued)

FOREIGN PATENT DOCUMENTS

| EP | 0216149 | 4/1987 |
|---|---|---|
| EP | 0308102 | 3/1989 |

(Continued)

OTHER PUBLICATIONS

Chemistry Grads Post Gains in 2005, ACS News, C&EN Jul. 24, 2006.*

*Primary Examiner* — James Rogers
(74) *Attorney, Agent, or Firm* — Jeffrey R. Ramberg

(57) ABSTRACT

Porous polymers having a plurality of openings or chambers that are highly convoluted, with each chamber being defined by multiple, thin, flat partitions are produced by a new gel enhanced phase separation technique. In a preferred embodiment, a second liquid is added to a polymer solution, the second liquid causing the solution to increase in viscosity. With sufficient polymer and second liquid present, the increase in viscosity can be up to that of a gel. The gel can then be shaped as needed. Subsequent solvent extraction leaves the porous polymeric body of defined shape. The porous polymers have utility as medical prostheses, the porosity permitting ingrowth of neighboring tissue. A second material may be incorporated into the chambers, thereby creating a microstructure filling the voids of the macrostructure. A porous polymeric body manufactured by this process may incorporate biologically active agents, and which agents may be delivered in a time-staged delivery manner, where differing drugs may be delivered over differing periods.

6 Claims, 7 Drawing Sheets

(56) References Cited

U.S. PATENT DOCUMENTS

| | | | |
|---|---|---|---|
| 5,447,724 A * | 9/1995 | Helmus et al. | 424/426 |
| 5,462,704 A | 10/1995 | Chen et al. | |
| 5,508,036 A | 4/1996 | Bakker et al. | |
| 5,549,860 A | 8/1996 | Charlesworth | |
| 5,609,624 A | 3/1997 | Kalis | |
| 5,609,629 A | 3/1997 | Fearnot et al. | |
| 5,700,287 A | 12/1997 | Myers et al. | |
| 5,716,395 A | 2/1998 | Myers et al. | |
| 5,744,515 A | 4/1998 | Clapper | |
| 5,747,128 A | 5/1998 | Campbell et al. | |
| 5,756,035 A | 5/1998 | Underwood et al. | |
| 5,863,627 A | 1/1999 | Szycher et al. | |
| 5,876,452 A | 3/1999 | Athanasiuo et al. | |
| 5,939,323 A | 8/1999 | Valentini et al. | |
| 5,977,223 A | 11/1999 | Ryan et al. | |
| 6,013,853 A | 1/2000 | Athanasiou et al. | |
| 6,296,667 B1 | 10/2001 | Johnson et al. | |
| 6,471,993 B1 | 10/2002 | Shastri et al. | |
| 6,685,697 B1 | 2/2004 | Arenberg et al. | |
| 6,726,923 B2 | 4/2004 | Iyer et al. | |
| 2002/0115197 A1 | 8/2002 | Ochi et al. | |

FOREIGN PATENT DOCUMENTS

| | | |
|---|---|---|
| EP | 0382356 | 8/1990 |
| EP | 0396809 | 11/1990 |
| EP | 0544259 | 6/1993 |
| EP | 0784985 | 7/1997 |
| JP | 50-042004 | 4/1975 |
| JP | 51-074058 | 6/1976 |
| JP | 58-189242 | 11/1983 |
| JP | 2000-319434 | 11/2000 |
| WO | WO-93/15694 | 8/1993 |
| WO | WO-94/09722 | 5/1994 |
| WO | WO-00/30564 | 6/2000 |
| WO | WO-00/55300 | 9/2000 |

* cited by examiner

METHOD FOR MAKING A POROUS POLYMERIC MATERIAL

CROSS-REFERENCE TO RELATED APPLICATIONS

This application is a Continuation in Part of U.S. patent application Ser. No. 10/864,143, filed on Jun. 9, 2004, entitled "Method for Making a Porous Polymeric Material", which was a Continuation in Part of U.S. patent application Ser. No. 10/856,329, filed on May 28, 2004 entitled Method for Making A Porous Polymeric Material, which is a continuation of U.S. patent application Ser. No. 10/010,304 filed on Nov. 8, 2001 entitled Method For Making A Porous Polymeric Material. This application is also a Continuation in Part of U.S. patent application Ser. No. 10/830,287 filed on Apr. 21, 2004 entitled Device For Regeneration Of Articular Cartilage And Other Tissue, itself a Continuation of U.S. patent application Ser. No. 10/199,961, filed Jul. 19, 2002, which is a continuation-in-part of U.S. patent application Ser. No. 09/909,027, filed Jul. 19, 2001, which is a continuation-in-part of U.S. patent application Ser. No. 09/206,604, filed Dec. 7, 1998, now U.S. Pat. No. 6,264,701, which is in turn a division of U.S. patent application Ser. No. 08/242,557, filed May 13, 1994, now U.S. Pat. No. 5,981,825. All of above listed patents and patent applications are assigned to the same assignee as this invention, and whose disclosures are incorporated by reference herein.

BACKGROUND OF THE INVENTION

1. Field of the Invention

The present invention relates to an improved porous polymer useful for various applications in industry, including the medical industry, for example, as a biological prosthesis and particularly useful in vascular surgery. The porous polymer can be made by use of a new gel enhanced phase separation technique, which, among other advantages, permits enhanced shape-making capability.

2. Discussion of Related Art

The present invention encompassing polymer engineering and processing came about from efforts to improve existing properties of porous polymers, including medical devices and prostheses and, in particular, medical devices (e.g., vascular grafts). Accordingly, a review of the vascular graft art is appropriate.

The search for the ideal blood vessel substitute has to date focused on biological tissues and synthetics. Despite intensive efforts to improve the nature of blood vessel substitutes many problems remain, such as increasing failure rate with decreasing caliber of the blood vessel substitute, a high failure rate when infection occurs, and aneurysm formation. The major need for vascular grafts is for adequate supply of blood to organs and tissues whose blood vessels are inadequate either through defects, trauma or diseases. Vascular grafts are also needed to provide access to the bloodstream for individuals undergoing hemodialysis. The three major types of vascular grafts are peripheral, arterial-to-venous access, and endovascular.

Peripheral grafts are those used in the neck and extremities, with the most common being used in the leg. This results in supply problems being some intermediate and most small diameter arteries are replaced or bypassed using an autologous saphenous vein, the long vein extending down the inside of the leg, with a secondary source being the radial veins of the arms. In a given patient, suitable veins may be absent, diseased or too small to be used, and removal of the vein is an additional surgical procedure that carries attendant risk.

Additionally, arterial-to-venous access grafts are used to access the circulatory system during hemodialysis. Vascular grafts used in connection with hemodialysis are attached to an artery at one end and sewn to a vein at the other. Two large needles are inserted into the graft. One needle removes the blood where it flows through an artificial kidney machine and is then returned to the body via the second needle. Normal kidney function is destroyed by several acute and chronic diseases, including diabetes and hypertension. Patients suffering from kidney failure are maintained by dialysis three times a week for approximately four hours per session. Due to the constant punishment these grafts undergo, there is a high occurrence of thrombosis, bleeding, infections, and pseudoaneurysm.

Endovascular grafts are used to reline diseased or damaged arteries, particularly those in which aneurysms have formed, in a less invasive manner than standard vascular surgical procedures. Various surgical techniques and materials have been developed to replace and repair blood vessels. Ideally, the thickness of the prosthesis is minimized, so that it can be delivered to the implantation site using a percutaneous procedure, typically catheterization and kept in place utilizing stents. Problems associated with this type of implantation include thrombosis, infection and new aneurysm formation at the location of the stent.

Initially, autografts were used to restore continuity; however, limited supply and inadequate sizes forced the use of allografts from both donor and umbilical cord harvest such as that described in U.S. Pat. No. 3,974,526. Development of aneurysms and arteriosclerosis as well as the fear of disease transmission necessitated the search for a better substitute.

Artificial vascular grafts are well known in the art. See for example U.S. Pat. No. 5,747,128; U.S. Pat. No. 5,716,395; U.S. Pat. No. 5,700,287; U.S. Pat. No. 5,609,624; U.S. Pat. No. 5,246,452 and U.S. Pat. No. 4,955,899. Development of two different fibrous and pliable synthetic plastic cloths revolutionized vascular reconstructive surgeries. Whenever suitable autograft was not available woven grafts of polyethylene terephthalate (Dacron®) and drawn out polytetrafluoroethylene (Teflon®) fibrils as defined in U.S. Pat. Nos. 3,953,566; 4,187,390 and 4,482,516 were used. Even though these products were widely used they did have many drawbacks including infection, clot formation, occlusions and the inability to be used in grafts smaller than 6 mm inside diameter due to clotting. Additionally, the graft had to be porous enough so that tissue ingrowth could occur, yet have a tight enough weave to the fibers so that hemorrhage would not occur. This made it necessary to pre-clot these grafts prior to use. Recently, vascular prostheses have been coated with bioabsorbable substances such as collagen, albumin, or gelatin during manufacture instead of preclotting at surgery. For purposes of this patent disclosure, the term "bioabsorbable" will be considered to be substantially equivalent to "bioresorbable", "bioerodable", "absorbable" and "resorbable".

Compliance problems with woven polyethylene terephthalate and drawn out polytetrafluoroethylene prompted interest in thermoplastic elastomers for use as blood conduits. Medical grade polyurethane (PU) copolymers are an important member of the thermoplastic elastomer family. PU's are generally composed of short, alternating polydisperse blocks of soft and hard segment units. The soft segment is typically a polyester, polyether or a polyalkyldoil (e.g., polytetramethylene oxide). The hard segment is formed by polymerization of either an aliphatic or aromatic diisocyanate with chain extender (diamine or glycol). The resulting product containing the urethane or urea linkage is copolymerized with the soft segment to produce a variety of polyurethane formulations. PU's have been tested as blood conduits for over 30 years. Medical grade PU's, in general, have material properties that make it an excellent biomaterial for the manufacture of vascular grafts as compared to other commercial plastics. These properties include excellent tensile strength, flexibility, toughness, resistance to degradation and fatigue, as well as biocompatiblity. Unfortunately, despite these positive qualities, it became clear in the early 1980s that conventional ether-based polyurethane elastomers presented long-term biostabilty issues as well as some concern over potential carcinogenic degradation products. Further, in contrast to excellent performance in animal trials, clinically disappointing results with PU-based grafts diminished the attractiveness of the material for this application.

Recent developments in new generation polyurethanes, however, have made this biomaterial, once again, a promising choice for a successful long-term vascular prosthesis. Specifically, the new generation of polyurethanes solved the biostability problems but still provide clinically disappointing results. Poor performance is largely due to limitations of current manufacturing techniques that create a random or non-optimal fibrous structure for cell attachment using crude precipitation and/or filament manufacturing techniques. (See, for example, U.S. Pat. Nos. 4,173,689; 4,474,630; 5,132,066; 5,163,951; 5,756,035; 5,549,860; 5,863,627 & International Patent Publication WO 00/30564)

Nonwoven or non-fibrous polyurethane vascular grafts have also been produced, and various techniques have been disclosed for swelling and/or gelling polyurethane polymers.

U.S. Pat. No. 4,171,390 to Hilterhaus et al. discloses a process for preparing a filter material that can be used, for example, for filtering air or other gases, for filtering gases from high viscosity solutions, or for preparing partially permeable packaging materials. A first solution containing an isocyanate adduct dissolved in a highly polar organic solvent is admixed into a second solution containing a highly polar organic solvent and a hydrazine hydrate or the like. The first solution is admixed into the second solution over an extended period of time, during which time the viscosity of the admixture increases as the hydrazine (or the like) component reacts with the isocyanate to produce a polyurethane. The first solution is added up to the point of instantaneous gelling. The final admixture is coated onto a textile reinforcing material, and the coated material is placed in a water bath to coagulate the polyurethane. The resulting structure features a thin, poreless skin that must be removed, for example, by abrasion, if the structure is to be useful as a filter.

U.S. Pat. No. 4,731,073 to Robinson discloses an arterial graft prosthesis comprises a first interior zone of a solid, segmented polyether-polyurethane material surrounded by a second zone of a porous, segmented polyether-polyurethane, and usually also a third zone surrounding the second zone and having a composition similar to the first zone. The zones are produced from the interior to the exterior zone by sequentially dipping a mandrel into the appropriate polymeric solution. The porous zone is prepared by adding particulates such as sodium chloride and/or sodium bicarbonate to the polymer resin to form a slurry. Once all of the zones have been formed on the mandrel, the coatings are dried, and then contacted to a water bath to remove the salt or bicarbonate particles.

U.S. Pat. No. 5,462,704 to Chen et al. discloses a method for making a porous polyurethane vascular graft prosthesis that comprises coating a solvent type polyurethane resin over the outer surface of a cylindrical mandrel, then within 30 seconds of coating, placing the coated mandrel in a static coagulant for 2-12 hours to form a porous polyurethane tubing, and then placing the mandrel and surrounding tubing in a swelling agent for 5-60 minutes. After removing the tubing from the mandrel, the tubing is rinsed in a solution containing at least 80 weight percent ethanol for 5-120 minutes, followed by drying. The coagulant consists of water, ethanol and optionally, an aprotic solvent. The swelling agent consists of at least 90 percent ethanol. The resulting vascular graft prosthesis features an area porosity of 15-50 percent and a pore size of 1-30 micrometers.

U.S. Pat. No. 5,977,223 to Ryan et al. discloses a technique for producing thin-walled elastomeric articles such as gloves and condoms. The method entails dipping a mandrel modeling the shape to be formed into a coagulant solution, then dipping the coagulant coated mandrel into an aqueous phase polyurethane dispersion, removing the mandrel from the dispersion, leaching out any residual coagulant or uncoagulated polymer, and finally curing the formed elastomeric article. When the polyurethane dispersion comprises by weight about 1 to 30 parts per hundred of a plasticizer based on the dry polyurethane weight, the dispersed polyurethane particles swell. Thus, if the dispersion featured polyurethane particles having a mean size between 0.5 and 1.0 micrometer in the unplasticized condition, they might be between 1.5 and 3.0 micrometers in the plasticized condition. The inventors discovered that such swollen polyurethane particles produce a superior product, whereas in an unplasticized condition, particles of such a size (1.5-3.0 micrometers) impede uniform drying because of the large interstitial space between particles. Preferred coagulants are ionic coagulants such as quaternary ammonium salts; preferred plasticizers are the phthalate plasticizers.

U.S. Pat. No. 3,492,154 to Einstman et al. discloses a technique for making a microporous sheet, useful as an artificial leather material. Einstman dissolves a polymer such as polyurethane in a solvent to make a solution, coats the solution onto a porous substrate, and then plunges the coated substrate into a liquid that coagulates the polymer. The solvent preferably is miscible in the coagulant. The coagulant is a non-solvent such as water, methanol, benzene or chloroform. Important to a high quality product is rapid coagulation of solid polymer from solution, and Einstman accomplishes this by dropping the temperature of the coated substrate by at least 10 C during coagulation, and also by adding a quantity of the non-solvent to the polymer solution prior to quenching. The quantity is not enough to cause coagulation at the higher temperature, but rather is about 70 to 98% of this quantity.

U.S. Pat. No. 3,553,008 to Reischl et al. is also concerned with producing leather-like sheets. To carry out his process, Reischl dissolves polyurethane in a solvent. As with Einstman, Reischl adds a quantity of non-solvent to his solution, preferably not enough to cause gel formation, but preferably at least 60% of this quantity. The non-solvent should be miscible with the solvent. The solution is then applied to a substrate, which can be either porous or non-porous. The solvent and non-solvent are then evaporated, leaving behind solid, microporous polyurethane.

U.S. Pat. No. 5,077,049 to Dunn discloses injecting a polymeric solution into the human body. The solvent for the polymer is water-miscible, so upon contact with aqueous saline solution (e.g., body intercellular fluid), the latter extracts the solvent. As is disclosed in other prior art documents, this contact with aqueous solution coagulates the polymer, thereby forming a solid or gelatinous implant. Dunn discloses a long list of candidate solvents, as well as a long list of polymers. Dunn goes on to explain that not all of his listed solvents will dissolve every polymer listed (col. 5, lines 52-58). There is some overlap among the liquids disclosed by Dunn, and those of the present invention. However, there is no disclosure in Dunn of mixing or combining solvents, let alone a disclosure or suggestion of applying liquids in sequential fashion to gel a polymer solution. Dunn uses water for his gelation step, water being a well-known non-solvent (his claim reads "water-coaguable).

In each instance, there are severe shape-making limitations, e.g., the known non-fibrous methods appear to be limited to working with a relatively low viscosity liquid that can be coated onto a surface, or into which a shape-forming mandrel can be dipped. It would be desirable if the polymer could be rendered in the form of a gel because a gel, inter alia, can be molded, such as being extruded. In other words, the gel can be plastically shaped and can retain its molded shape without reverting to its original shape. Usually the molded shape is preserved so that the shaped polymer retains the new shape and will return to the new shape if deformed, provided that the elastic limit is not exceeded. Further, most of the above-discussed non-fibrous art results in a product that features a non-porous layer at least at some location in the product. Thus, the prior art does not seem to appreciate the desirability of a prosthesis such as a vascular graft containing channels or porosity extending continuously from the exterior surface to the luminal surface of the graft.

One of the reasons for failure of vascular grafts is due to the formation of acute, spontaneous thrombosis, and chronic intimal hyperplasia. Thrombosis is initiated by platelets reacting with any non-endothelialized foreign substance, initiating a platelet agglomeration or plug. This plug continues to grow, resulting in occlusion of the graft. If the graft is not immediately occluded the plug functions as a cell matrix increasing the potential for rapid smooth muscle cell hyperplasia. Under normal circumstances, platelets circulate through the vascular system in a non-adherent state. The endothelial cells lining the vascular system accomplish this. These cells have several factors that contribute to their non-thrombogenic properties. These factors include, but are not limited to, negative surface charge, the heparin sulfate in their glycocalyx, the production and release of prostacylin, adenosine diphosphate, endothelium derived relaxing factor, and thrombomodulin. Thus, adherence of a thin layer of endothelial cells to the vascular prosthetic results in enhanced healing times and reduced failure rates of the graft.

Other reasons for artificial graft failure are neointima sloughing due to poor attachment and aneurysm formation resulting from compliance mismatch of the new graft material to the existing vascular system. It is important to know that materials with different mechanical properties, when joined together and placed in cyclic stress systems, exhibit different extensibilities. This mismatch may increase stress at the anastomotic site, as well as create flow disturbances and turbulence. Additionally, poor attachment geometry can lead to the problematic results above, due to flow disturbances and turbulence. For example, the harvesting of autograft veins typically causes a surgeon to use a graft of non-optimal diameter or length. A graft diameter mismatch, of perhaps 60% or more, causes a drastic reduction in flow diameter. Such flow disturbances may lead to para-anastomotic intimal hyperplasia, anastomotic aneurysms, and the acceleration of downstream atherosclerotic change.

Finally, artificial graft failures have been linked to leaking of blood through the device. Pre-clotting and the addition of short-lived bioabsorbable substances such as collagen, gelatin and albumin can prevent this as well as provide a matrix for host cell migration into the prosthesis. One problem with this approach is that the same open fibrous weave that permits blood leaking also allows the viscous bioabsorbable substances and clotted blood to accumulate on the luminal surface and easily detach resulting in complications (e.g., emboli) downstream from the device.

SUMMARY OF THE INVENTION

The present invention manufactured through a novel gel enhanced phase separation technique solves the above listed problems that occur in existing vascular prostheses, both fibrous and non-fibrous.

According to the method of the present invention, a porous polymer is prepared by dissolving the polymer in a solvent and then adding a "gelling solvent". The "gelling solvent" for the polymer is not to be confused with a "non-solvent", which is a substance that causes the polymer to precipitate out of solution. The non-solvent is sometimes referred to interchangeably as the "coagulant" or the "failed solvent". The "gelling solvent" similarly has a number of different synonyms, largely depending on the conditions under which it is used; accordingly, a brief discussion of terminology is in order. Unless indicated otherwise, for purposes of this invention, the liquid that dissolves the polymer to form a polymer solution is interchangeably referred to as the dissolving solvent or first solvent. The liquid that causes substantial swelling of, but not dissolution of, solid polymer is most often referred to as the "swelling solvent" or "swelling agent". When this same substance causes a polymer in solution to thicken and ultimately to gel, it is referred to as a "gelling solvent" or "gelling agent".

Significantly, when a "gelling agent" is added to a polymer/solvent solution, the polymer does not precipitate out as it would with a "non-solvent", which would leave two distinct phases. Instead, the entire volume of dissolved polymer solution begins to thicken as the dissolved polymer absorbs the gelling agent. Significantly, no visible phase separation occurs, and the entire solution remains transparent. As more gelling agent is added, the viscosity of the entire volume increases to the point where it becomes a gelatinous mass that can be picked up, e.g., a stable gel. This gel can then be spread out onto plates or transferred into molds. The plates or molds can then be immersed into a non-solvent that leaches the first solvent from the gel or placed under vacuum to pull the solvent from the gel, leaving an intercommunicating porous network. The unit is then cured for several hours in an oven to permanently set the architecture. Varying the concentration of polymer in the first solution and/or the concentration of the "gelling agent" added will reproducibly alter the porosity. Polymers useful for the creation of the finished article (e.g., a tubular prosthesis) include but are not limited to the following groups: a) polyurethanes; b) polyureas; c) polyethylenes; d) polyesters; and e) fluoropolymers.

The articles created using this technique include, but are not limited to, a non-metallic, non-woven, highly porous graft material having an inner surface and an outer surface, and having a plurality of openings throughout its bulk providing a highly convoluted intercommunicating network of chambers between its two surfaces, the walls of the chambers providing a large surface area. In part, it is this highly porous, convoluted intercommunicating network of chambers that allows the present invention to overcome problems that have plagued previous vascular grafts.

In another aspect of the present invention, other bioabsorbable substances can be impregnated into the chambers of the device and be protected from the circulating blood. In a preferred embodiment, it may be beneficial to incorporate the bioabsorbable substance into the chambers as a liquid and freeze-dry it to form a microstructure within the macrostructure consisting of the chambers of the device. Representing yet another important aspect of the present invention, an additional benefit of the microstructure isolation within the intercommunicating chambers is the ability to carry and retain one or more biologically active agents within the article or prosthesis. In certain applications, it may also be necessary to provide a burst release or a delayed release of the active agent, that is, a time-staged delivery of active agent.

Typical of past practice was to partially precipitate the polymer from solution, or to add a leachable solid such as a salt, in order to produce a porous polymeric body. The creation of a stable gel that can be injected into finely detailed molds without risk of clumping of the precipitate or salt, is a vast improvement over existing technologies. This gel will open up the possibility of mass production of complex prostheses, including heart valve, bladder, intestinal, esophagus, urethra, veins and arteries, via an automated system. Additionally, articles produced through the practice of this invention include larger components, with complicated geometries, and unique density-property-processing relationships; of which, these articles may be used in various industries (e.g., automotive, consumer goods, sporting goods, etc.).

DETAILED DESCRIPTION OF THE INVENTION AND PREFERRED EMBODIMENTS

Figure 1:
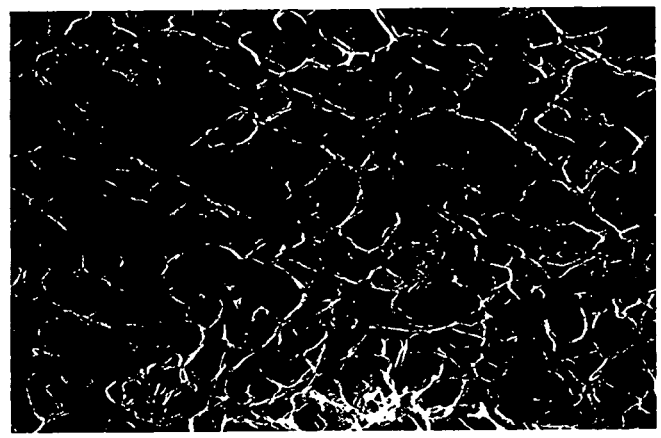
FIGS. 1-10 are Scanning Electron Microscope (SEM) images of four different vascular grafts made from four different species of polymer using the gel enhanced phase separation technique.

While working with several different species of polymer, a new and unique method for controlled incorporation of intercommunicating pores within the polymers was discovered. In a preferred embodiment, the method for preparing the porous polymers involves dissolving the polymer in a first solvent (the dissolving solvent) and then adding a gelling agent or "gelling solvent". The "gelling solvent" for the particular polymer is not to be confused with a "non-solvent" that causes the polymer to precipitate out of solution. Solid polymer particles placed in contact with a liquid gelling solvent swell as they absorb the liquid and take on fluid like properties. However, the polymer particles do not lose cohesiveness, but instead remain as discrete, albeit swollen particles.

A common example of this phenomenon exists in the polymers used to make soft contact lenses. Hydroxyethylemethacrylate (HEMA) can achieve water contents ranging from 35% to 75% when immersed. The water is absorbed into this solid brittle polymer and transforms it into a swollen soft mass. Water functions as a gelling solvent for this polymer. Liquids that cause this swelling of solid polymer are candidate substances that cause gelation of the polymer in solution form.

In accordance with the present invention, when a gelling solvent (i.e., "gelling agent") is added to a polymer/solvent solution, the polymer does not precipitate out as it would with a "non-solvent", which would form two separate phases. Instead, the entire volume of solution begins to thicken as the dissolved polymer absorbs the gelling agent. As more gelling agent is added, the viscosity increases, eventually reaches a maximum, and then decreases with continued increasing amounts of gelling agent, as the system becomes more and more dilute in polymer. But with sufficient polymer concentration and an appropriate amount of gelling agent, the whole mass, the entire volume of solution, turns into a gelatinous mass that can be picked up. If the beginning polymer/solvent volume was 20 ml, and 20 ml of gelling agent were added, the result would be 40 ml of gel. This is in distinct contrast to the prior art techniques whereby gelation is induced by a non-solvent. There, the non-solvent causes phase separation, and the gel is a precipitate; it is not the entire volume that is gelled. Moreover, typically only a few percent addition of the non-solvent to the solution is sufficient to cause the precipitation/gelation phenomenon.

This gel can then be shape-formed, e.g., molded, for example, by spreading or injecting the gel over a plate or a three-dimensional object, or by forcing a plate or three-dimensional object into the gel. Further shape molding could be accomplished by extruding the gel into a near-final shape (e.g., a tubing suitable for vascular graft bypass surgery). The extrusion process would allow increased production, reduced costs, reduced waste, and more consistent final devices.

The plates, molds, or extruded tubing can then be immersed into a non-solvent that leaches the original solvent from the gel. Alternatively, the plates, molds, or extruded tubing may be placed under vacuum to pull the solvent from the gel, leaving an intercommunicating porous network. The unit is then cured for several hours in an oven to permanently set the architecture. (In most cases the gelling agent is also removed in the leaching or vacuum process.) Varying the polymer concentration in the original solution and/or varying the concentration of the "gelling agent" added will reproducibly alter the porosity. For example, the lower the concentration of polymer, the more porous is the final product. Polymers useful for the creation of the final article include but are not limited to the following groups: a) polyurethanes; b) polyureas; c) polyethylenes; d) polyesters; and e) fluoropolymers.

In contrast to the present invention, the gelations of Einstman and Reischl, in keeping with the characteristics of non-solvent induced precipitations, do not cause the gelation of the entire volume of solution. Rather, they cause the separation of the solution into two distinct phases, one of the phases being gelatinous, and the other being of lower viscosity, sometimes described as a serum. Again, Reischl noted that his gel had an opaque character.

As will be discussed in more detail to follow, a given liquid typically will not universally behave as a solvent or a gelling agent; it depends, for example, on the nature of the polymer being processed. Accordingly, the present invention acknowledges that one may have to perform some tests, albeit simple and quick screening procedures, to classify the action of a given liquid on a polymer and thus to identify its role. Further, there are a few "rules of thumb" or general approximations that are helpful in identifying appropriate liquids as the solvent and gelling agent. Accordingly, the present inventor has developed a quick and easy screening technique, a "protocol"

for rapidly identifying by simple, routine experimentation, which liquids will function as the solvent and gelling agent, respectively, for a given polymer.

The screening protocol consists essentially of contacting small samples of solid polymeric material to a candidate liquid and observing the results. Liquids that can completely dissolve the solid polymer are obviously candidate solvents. In the case of commercially obtained solid polymer, the manufacturer often provides this information. Candidate gelling agents are those liquids that do not dissolve solid polymer, but rather are taken up or absorbed by the solid polymer, and in substantial, non-trivial quantities, for example, on the order of at least about 35 percent, and often at least about 50 percent, and perhaps about 75 percent by weight, and sometimes even more.

A liquid that functions as a non-solvent in a polymer system behaves differently from a gelling agent. Although there are isolated disclosures in the prior art (Reischl, for example) of a polymer absorbing 50% of its mass in the form of a non-solvent like water, typically, a non-solvent is absorbed very little into a polymer. By "absorbed", what is meant is that the liquid is taken up into the solid structure of the polymer and liquid molecules occupy space between polymer molecules. It does not refer to the absorption typical of a sponge, where liquid is taken up into the (macroscopic) pore space of the sponge.

The articles created using the techniques of the present invention include a non-metallic, non-woven highly porous graft material having a plurality of openings throughout its substance providing a highly convoluted intercommunicating network of chambers between its two surfaces, the walls of the chambers are defined by multiple, thin, flat partitions, thereby providing a large surface area. In part, it is this highly porous, convoluted intercommunicating network of chambers that allows the present invention to overcome problems that have plagued previous vascular grafts, and further offers unique properties useful to the various aforementioned industries and product types.

Similar appearing technologies that utilize simple phase separation/precipitation in non-solvents or leaching of solid particles such as salt are difficult if not impossible to reproduce on a large scale due to their demand for constant skilled human interaction. Additionally they are limited in the final conformation of medical device formed. The creation of a stable gel, which can be injected into finely detailed molds without risk of clumping of the precipitate or salt, is a vast improvement over existing technologies. This gel will open up the possibility of mass production of complex articles such as, for example, prostheses, including heart valve, bladder, intestinal, esophagus, urethra, veins and arteries, via an automated system. A specially designed press can be used for injection of the gel into custom molds containing wings, flaps, ribs, waves, multiple conduits, appendages or other complex structures unavailable to prior art devices. The molds will then move to an immersion and/or vacuum chamber to remove the dissolving solvent and "gelling solvent", after which the devices are placed into a curing oven.

Composite or multifaceted materials can be fabricated by placing the gel in contact with one or more other materials. Examples of such other materials include, but are not limited to, biologically active agents, and biodegradable or non-degradable particulates, sutures or fibers, one or more reinforcement rings, one or more stents, screens, meshes, connectors. The gel could be, for example, injected over a suture, or injected into a mass of fibers. Additionally, two different gels composed of different polymer concentrations or polymers can be layered on top of or mixed with each other to create laminates and composites previously unknown. At this point, at least the gel portion of the resulting mass is still shapeable (e.g., moldable), and accordingly can be shaped by known techniques to the desired geometry. The solvent is then removed as described previously, leaving the porous polymer material and the other material mechanically attached to one another. The resulting composite body could represent the entire article, or it could be merely a component of a larger article (e.g., an entire prosthesis or simply a component thereof).

As suggested by the above embodiment of injecting the gel into a mass of fibers, one or more reinforcement materials (e.g., particulate, fibers, whiskers, screens, meshes, woven materials, etc.) may be incorporated or admixed with the present polymers by known techniques. A very typical reason for incorporating such a reinforcement (but by no means the sole reason) is to enhance certain physical properties such as strength, stiffness, etc.

In the prosthesis embodiment of the invention, it is the intent to allow uninterrupted tissue connection, e.g., contiguous tissue, to exist throughout the entire volume of the prosthesis. Thus when a neointima forms across the lumen of the prosthesis, it is not only attached to the surface of the graft material, but additionally anchored to the tissue growing through the prosthesis. Once fully integrated with tissue, the graft is hidden by the newly formed endothelial cell lining from the blood flowing through it and thus benefits from the endothelial cells' non-thrombogenic properties.

Additionally, the material produced by this preferred teaching of the present invention may occupy only a small fraction of the overall volume of the device. This allows the tissue within the device to dictate the mechanical properties of the device preventing a compliance mismatch of the graft material to the existing vascular system.

Figure 12:
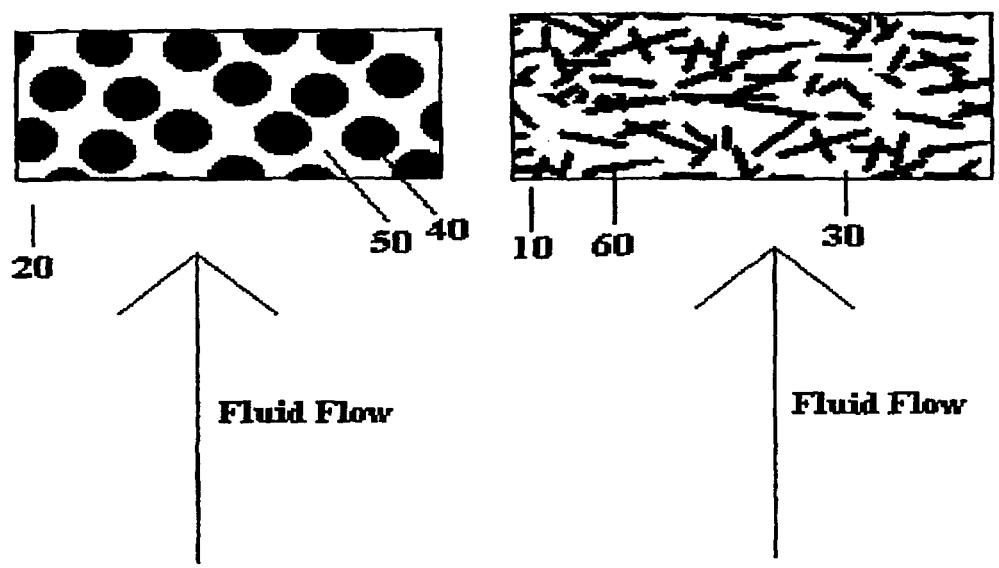
FIG. 12 is a schematic illustration of the polymeric microstructure in the prior vascular grafts (right drawing) versus the polymeric microstructure in the vascular grafts of the present invention (left)

Finally, the unique arrangement of intercommunicating chambers 30 within the device 10 manufactured by the process of the present invention prevents leaking of blood through the device by slowing the movement of blood through the thickness of the unit many times over, allowing it to clot and self-seal. The fibrous structure 50 in state of the art grafts 20 provides rounded cylinders 40 throughout the mass of the device (see FIG. 12, left side). These cylinders provide a low surface area and thus relatively low resistance to flow. To compensate for this, the density of cylindrical fibers 40 must be increased, reducing the overall porosity of the unit. The present invention overcomes this by providing thin flat plates 60 of polymer material having a relatively large surface area to disrupt flow through the chambers 30 defined by the flat surfaces (FIG. 12, right). The large surface area of each individual chamber slows the movement of blood, creating small interconnecting clots. These clots are then trapped within the internal chambers of device and cannot be sloughed off into the blood stream.

In another aspect of the present invention, other bioabsorbable substances can be impregnated into the chambers of the device and be protected from the circulating blood. For example, it may be beneficial to incorporate the bioabsorbable substance into the chambers to coat the interior surface of the chambers. In a preferred embodiment of the present invention, it may be beneficial to incorporate the bioabsorbable substance into the chambers as a liquid and freeze-dry it to form a microstructure within the macrostructure consisting of the chambers of the device. A microstructure created as described may fill the chambers of the macrostructure and form a separate structural element (e.g., plates, etc.) contained within voids, but largely independent, separate and distinct of the macrostructural chambers, such that the structural element of the microstructure only incidentally contacts the macrostructure. A microstructure created as described, however, further lacking the ability to be self-supporting, may collapse against the macrostructure void surfaces, thereby creating a coating thereupon. The microstructure, particularly if it is soluble in tissue fluids, can then be cross-linked or in some other way stabilized so that it typically must be degraded to be removed from the prosthesis. Incorporation of the stabilized microstructure can then be used to fine-tune the properties of the graft to that of the host vessel. The purpose of the microstructure is at least four-fold: (i) provide a temporary pore seal to further increase resistance to flow through the thickness of the unit; (ii) increase the biocompatibilty of the overall prosthesis for cellular attraction and attachment; (iii) provide for control of mechanical properties other than via concentration of constituents of the gel-enhanced phase separation process; and (iv) provide a medium for the delivery of biologically active agents to, for example, mediate or moderate the host response to the implant graft.

Useful bioabsorbable substances include collagen, gelatin, succinylated collagen, chondroitin sulfate, succinylated gelatin, chitin, chitosan, cellulose, dextran, fibrin, albumin, alginic acid, heparin, heparan sulfate, dermatin sulfate, keratan sulfate, hyaluronic acid, termatan sulfate, polymerized alpha hydroxy acids, polymerized hydroxy aliphatic carboxylic acids, polymerized glycolic acids and derivatives of these members.

Representing yet another important aspect of the present invention, an additional benefit of the microstructure isolation within the intercommunicating chambers is the ability to carry and retain one or more biologically active agents within the article or prosthesis. The biologically active agents can promote healing and tissue invasion, and are protected from the flowing blood. Additionally, the microstructure may be formed from polysaccharides and chemotactic ground substances with biologically beneficial properties, such as encouraging cell ingrowth. A biologically active agent may be defined to include a plurality of substances arranged to be delivered contemporaneously, and may include physiologically acceptable drugs (e.g., table 1), surfactants, ceramics, hydroxyapatites, tricalciumphosphates, antithrombogenic agents, antibiotics, biologic modifiers, glycosaminoglycans, proteins, hormones, antigens, viruses, cells and cellular components. The biologically active agent can be added to the microstructure before or after cross-linking. The biologically active agents can be chemically bound to the microstructure, and may be released as the microstructure is resorbed. Moreover, the biologically active agent can be added during the gel enhanced phase separation process for producing the porous polymeric material. For example, the biologically active agent can be mixed with the polymer and first solvent prior to addition of the gelling solvent; it can be mixed with the gelling solvent prior to addition of the gelling solvent to the polymer/first solvent solution; or it can be mixed with the gel prior to removal of the solvents. Still further, the biologically active agent can be incorporated within the pores of the polymeric material after removal of the solvents.

In certain applications, it may also be necessary to provide a burst release or a delayed release of the active agent. The device may also be designed to deliver more than one agent at differing intervals and dosages, this time-staged delivery also allows for a dwell of non-delivery (i.e., a portion not containing any therapy), thereby allowing alternating delivery of non-compatible therapies. Delivery rates may be affected by the amount of therapeutic material, relative to the amount of resorbing structure, or the rate of the resorption of the structure.

In an embodiment featuring a time-staged delivery or tiered delivery of biologically active agents or therapies, at least one biologically active agent or therapy may be released from the microstructure at a first rate, thereby causing a first response. Subsequently, at least one different biologically active agent or therapy associated with the macrostructure by being, for example, chemically bound or more preferably, physically entrapped within the porous macrostructure of the device, may be released from the macrostructure at a second rate, thereby causing a second response. In the two tier system described above, preferably the delivery of each of the biologically active agents from the microstructure and macrostructure is largely sequential, whereupon substantially all of the agent incorporated into the microstructure is delivered to the living being before a substantial portion of the agent incorporated into the macrostructure is delivered. Through this time-staged delivery of biologically active agents, the delivery of biologically active agents with differing activities or effects may be efficiently accomplished.

For example, where an implantable device of the present invention has been inserted to effectuate healing of a bone wound, the device featuring sequential delivery may deliver a first biologically active agent (e.g., drugs, cells, cartilage directed growth factors, etc.) which cause a response by the body, here the growth or promotion of a first type of tissue (e.g., fibrillar cartilage, etc.).

Subsequently, the delivery of a second biologically active agent (e.g., drugs, bone directed growth factors, etc.), the body may in response grow or promote a second type of tissue (e.g., calcified bone).

Alternatively, after implantation of the device of the present invention as a vascular graft, an anti-coagulant drug that reduces the occurrence of blood clotting (e.g., heparin, etc.) may be delivered from the microstructure. During this period, the body's healing response (e.g., neointima growth, etc.) would occur, with the impediments and dangers of unwanted blood clotting reduced by the delivery of the first biologically active agent. Subsequently, after all or substantially all of the first biologically active agent has been delivered, a second biologically active agent (e.g., heparin and sirolimus) may be released from the macrostructure, in order to prevent hyperplasia and unwanted blood clotting.

Due to the nature of sequential or tiered delivery, it becomes possible to deliver first and second biologically active agents that cause opposite or contradictory responses, without risking harm to the patient or ineffectiveness of either drug due to the net effects of each drug being at least partially cancelled out by the other, as would occur where both biologically active agents released contemporaneously.

In an embodiment, the device may deliver first and second biologically active agents, each designed to generate a response. The living being may manifest a biological response upon introduction of the first biologically active agent, and subsequently, the second biologically active agent may result in the living being generating a completely opposite biological response.

For example, after implantation of the device of the present invention as a vascular graft, a drug that encourages the cell proliferation, differentiation, and/or growth (e.g., growth factors, VEGF, PDGF, retinoic acid, ascorbic acid, aFGF, bFGF, TGF-alpha, TGF-beta, Epidermal GF, Hepatocyte GF, IL-8, Platelet Activating Factor, Granulocyte-colony stimulating Factor, Placental GF, Ploriferin, B61, Soluble Vascular Cell Adhesion Molecule, Soluble E-selectin, 12-hydroxyeicosatetraenoic acid, Angiogenin, TNF-alpha, Prostaglandin, Fas ligand, etc.) may be delivered, thereby facilitating the differentiation and growth of endothelial cells to form a healthy neointima. Subsequently, and after all or nearly all of the first drug has been delivered, a second drug with anti-proliferative properties (e.g., sirolimus, cyclosporin-a, tacrolimus, paclitaxel, cisplatin, Actinomycin-D, L-nitro arginine methyl ester, mycophenolate mofetil, TP53 (tumor suppressor gene), RB, VHL, Thrombospondin-1 (TSP-1), Angiostatin, Endostatin, spliced HGH, PF4, Interferon-gamma, inducible protein 10(IP-10), gro-beta, IL-12, Heparinase, Proliferin related protein, 2-methoxyoestradiol, etc.) may be delivered, in order to prevent a hyperplasic response due to excessive cell proliferation or growth. In this manner, an implanted vascular graft may, for a period after being implanted release a drug that facilitates the graft becoming invested with growing cells, and for a later period, releases a drug that prevents an overgrowth of cells, which if left unrestrained, would result in closing off the vessel.

In another embodiment of the device, the device may deliver first and second biologically active agents; each designed to generate a response. The response to the first biologically active agent may be an increase in some activity, whereupon upon subsequent introduction of the second biologically active agent, the activity may be lessened, such as being mitigated, reduced, or substantially terminated). In contrast to the previously described embodiment, the biological responses are not counter or opposite each other, rather an increase in an activity is reduced in scale. It is recognized that the activity may be have positive effects or negative effects. In other words, the first response may cause a negative activity increase (e.g., increases cell death, etc.) or alternatively, it may cause a positive activity increase (e.g., increased cell division and growth, etc.). The second active agent then serves to reduce the magnitude or intensity of the activity, such as by competitively binding the active sites or reagents needed for the activity, or otherwise making the activity unlikely.

In yet another embodiment of the device, a delayed response, for a period of time after implantation of the device, may be desirable before the delivery of a biologically active agent. The delay may beneficially allow a natural injury response to occur, thereby allowing the device to be incorporated properly with the surrounding tissue. Subsequently, when the release of the biologically active agent occurs, the injury response has already been initiated and/or completed without being affected by a substantial release of the biologically active agent.

For example, upon implantation of the device of the present invention as a vascular graft, a delay in delivery of an anti-proliferative agent or drug may be beneficial in allowing the body's natural healing response to form a neointima, during the formation of which substantially none of the anti-proliferative is delivered and available to interfere with that natural response. The delay may be created by temporarily isolating or insulating a drug or therapeutic agent from extensive contact with body fluids and tissue. This may be achieved, for example, through the incorporation of a microstructure in the device that, once implanted, absorbs body fluids, and prevents the body fluids from extensively contacting or flowing through the macrostructure surfaces. A microstructure suitable for insulating the biologically active agent from immediate release may be a hygroscopic and/or viscoelastic gel (e.g., Hyaluronic Acid, etc.). While preventing immediate release of the drug, the gel may still allow the passage of cells, nutrients, and wastes into and out of the pores of the macrostructure. Subsequently, an anti-proliferative drug, therapy, or biologically active agent (e.g., sirolimus, etc.) may then be released from the device, in order to prevent a hyperplasic response. Without incorporating the delay before delivery of the biologically active agent, the anti-proliferative would otherwise have prevented the growth and differentiation of cells, hindering the formation of a neointima.

It is recognized that there may be a benefit to the staged delivery of more than two tiers or time-stages of biologically active agents. By incorporating additional components (e.g. microspheres), and/or manipulating the molecular weight of the component polymers, and/or additional layers of material to the device, additional tiers of biologically active agents may be delivered sequentially.

The term "microsphere" is used herein to indicate a small additive that is about an order of magnitude smaller (as an approximate maximum relative size) than the implant. The term does not denote any particular shape, it is recognized that perfect spheres are not easily produced. The present invention contemplates elongated spheres and irregularly shaped bodies.

Microspheres can be made of a variety of materials such as polymers, silicone and metals. Biodegradable polymers are ideal for use in creating microspheres. The release of agents from bioresorbable microparticles is dependent upon diffusion through the microsphere polymer, polymer degradation and the microsphere structure. Although most any biocompatible polymer could be adapted for this invention, the preferred material would exhibit in vivo degradation. It is well known that there can be different mechanisms involved in implant degradation like hydrolysis, enzyme mediated degradation, and bulk or surface erosion. These mechanisms can alone or combined influence the host response by determining the amount and character of the degradation product that is released from the implant. The most predominant mechanism of in vivo degradation of synthetic biomedical polymers like polyesters, polyamides and polyurethanes, is generally considered to be hydrolysis, resulting in ester bond scission and chain disruption. In the extracellular fluids of the living tissue, the accessibility of water to the hydrolysable chemical bonds makes hydrophilic polymers (i.e. polymers that take up significant amounts of water) susceptible to hydrolytic cleavage or bulk erosion. Several variables can influence the mechanism and kinetics of polymer degradation, particularly, material properties like crystallinity, molecular weight, additives, polymer surface morphology, and environmental conditions. As such, to the extent that each of these characteristics can be adjusted or modified, the performance of this invention can be altered.

Examples of biologically active agents suitable for delivery, whether in a delayed or time-staged delivery embodiment or not, can be found in Table 1.

TABLE 1

Examples of Biologically Active Agents Deliverable via the Present Invention

Adenovirus with or without genetic material
Alcohol
Amino Acids
    L-Arginine
Analgesics
Angiogenic agents
Angiotensin Converting Enzyme Inhibitors (ACE inhibitors)
Angiotensin II antagonists
Anti-angiogenic agents
Antiarrhythmics
    Diltiazem
Anti-bacterial agents
Antibiotics
    Erythromycin
    Penicillin
    Ceftiofur
    Chlorotetracycline TABLE 1-continued Examples of Biologically Active Agents Deliverable
via the Present Invention Anti-coagulants
    Heparin
    Warfarin
Anti-growth factors
Anti-inflammatory agents
    Dexamethasone
    Ibuprofen
    Hydrocortisone
    Naproxen
    Indomethacin
    Nabumetone
Antioxidants
Anti-platelet agents
    Aspirin
    Clopidogrel
    Forskolin
    GP IIb-IIIa inhibitors
        eptifibatide
Anti-proliferation agents
    Rho Kinase Inhibitors
        (+)-trans-4-(1-aminoethyl)-1-(4-pyridylcarbamoyl)
        cyclohexane
Anti-rejection agents
    Sirolimus
    Tacrolimus
    Cyclosporine
Anti-restenosis agents
    Adenosine $A_{2A}$ receptor agonists
Antisense
Antispasm agents
    Lidocaine
    Nitroglycerin
    Nicarpidine
Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells/Cellular materials
    Adipose cells
    Blood cells
    Bone marrow
    Cells with altered receptors or binding sites
    Endothelial Cells
    Epithelial cells
    Fibroblasts
    Genetically altered cells
    Glycoproteins
    Growth factors
    Lipids
    Liposomes
    Macrophages
    Mesenchymal stem cells
    Progenitor cells
    Reticulocytes
    Skeletal muscle cells
    Smooth muscle cells
    Stem cells
    Vesicles
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-alpha)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interleukin-8 (IL-8)
Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39

TABLE 1-continued

Examples of Biologically Active Agents Deliverable
via the Present Invention

Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
    Atorvastatin
    Lovastatin
    Simvastatin
    Fluvastatin
    Pravastatin
Stem Cells
Steroids
Thrombin
Thrombin inhibitor
Thrombolytics
Ticlid
Tyrosine kinase Inhibitors
    ST638
    AG - 17
Vasodilators
    Histamine
    Forskolin
    Nitroglycerin
Vitamins
    E
    C
Yeast
Ziyphi fructus The inclusion of groups and subgroups in Table 1 is exemplary and for convenience only. The grouping does not indicate a preferred use or limitation on use of any drug therein. That is, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

The device of the present invention, in order to assure patient safety, may be manufactured in a sterile environment, however, in order to decrease manufacturing complexity and cost, the device may be terminally sterilized through standard sterilization techniques known in the art (e.g., plasma gas sterilization, gas sterilization, gamma irradiation, electron beam sterilization, steam sterilization, etc.).

Among the non-limiting advantages of using the present non-woven architectured synthetic implant instead of autograft or allograft as vascular grafts are the following:
1. sterile off-the-shelf implant;
2. availability of multiple diameter and length implants;
3. can be molded into unique shapes and designs to improve handling characteristics;
4. reduced risk of aneurysm;
5. no risk of disease transmission;
6. allows for easy ingrowth of fibrous tissue, which stabilizes and anchors the implant;
7. allows for vascular ingrowth (vasa vasorum) nourishing the graft and providing access to free floating stem cells;
8. the graft is straight, flexible and kink-resistant and can be twisted in any direction (this is a major advantage over autografts and allografts that must be implanted in their original shape to avoid complications);
9. allows for incorporation of bioabsorbable substances to improve biocompatibility;
10. allows for incorporation of biologically active agents to aid in healing; and
11. can be fabricated to have varying physical, chemical and mechanical properties along its length.

Among the non-limiting advantages of using the present non-woven architectured synthetic implant instead of present state-of-the-art woven or fibrous implants are the following:
1. interpenetrating pore structure allows for rapid but stable cellular ingrowth;
2. can be molded into unique shapes and designs to improve handling characteristics;
3. pore structure with large surface area reduces hemorrhage through the implant;
4. use of stabilized microstructure allows use of device with larger pore structure without hemorrhage risk;
5. creation of a living tissue barrier protects the material of the implant from coming in direct contact with blood flowing through the lumen;
6. allows for easy ingrowth of fibrous tissue which stabilizes and anchors the implant;
7. unbroken weave of tissue throughout device distributes stresses in an optimal manner, reducing occurrence of compliance mismatches;
8. allows for vascular ingrowth (vasa vasorum) which nourishes the graft and provides access to free floating stem cells;
9. pore structure allows the device to carry bioabsorbable materials without loss to circulatory system;
10. pore structure allows the device to support biologically active agents without dilution or loss to circulatory system; and
11. use of flat plates provides a greater surface area using less material allowing for a higher overall porosity.

Among the medical application areas envisioned for articles produced in accordance with the various teachings of the present invention include, but are not limited to, prostheses for use in vascular reconstructive surgery of mammals, including humans and other primates. The prosthesis may be used to repair, replace or augment a diseased or defective vein or artery of the body. The prosthesis may also be used as a substitute for the ureter, bile duct, esophagus, trachea, bladder, intestine and other hollow tissues and organs of the body. Additionally, the prosthesis may function as a tissue conduit, or, in sheet form it may function as a patch or repair device for damaged or diseased tissues. (e.g., heart, heart valves, pericardium, veins, arteries, stomach, intestine, bladder, dura, etc.) When functioning as a tissue conduit (e.g., nervous tissue) the lumen of the prosthesis may also carry substances that aid in tissue growth and healing.

In a preferred embodiment of the present prosthesis invention, namely that of a vascular graft, the graft consists of a polyurethane conduit composed of small chambers with each chamber being formed of multiple thin flat partitions. The thickness of each polymer partition is only a fraction of its length and height. This allows a small mass of polymer to create a large surface area providing high resistance to blood flow through the thickness of the prosthesis. One chief disadvantage of a highly porous vascular graft is its high permeability to blood during implantation leading to blood leakage through the graft wall. The unique arrangement of the intercommunicating chambers within the device of the present invention, however, reduces the leaking of blood by drastically slowing its movement through the thickness of the graft and allowing it to clot and self-seal.

Figure 2:
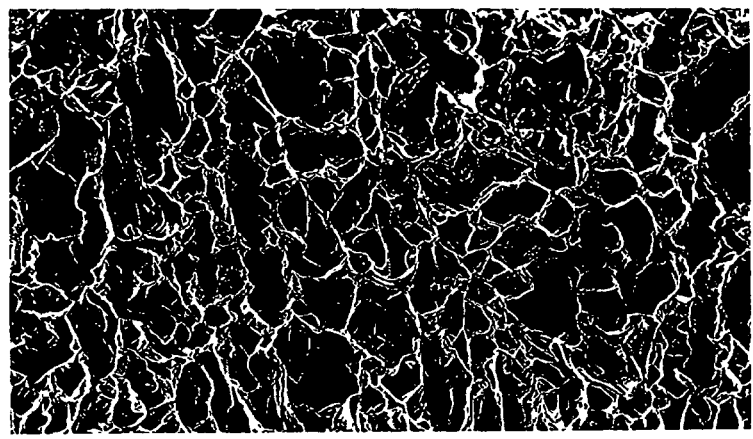
Figure 3:
Figure 4:
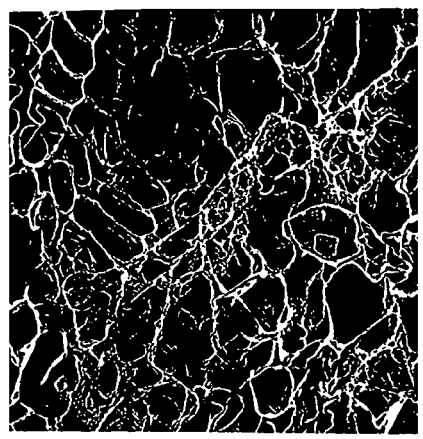
Figure 5:
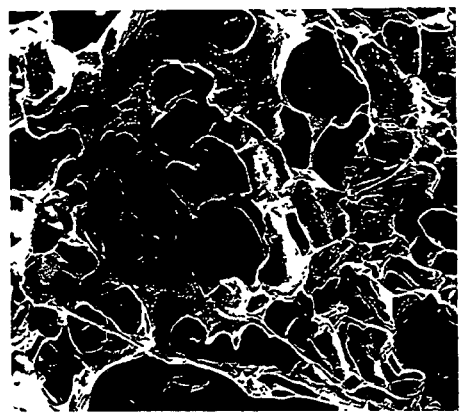
Figure 6:
Figure 7:
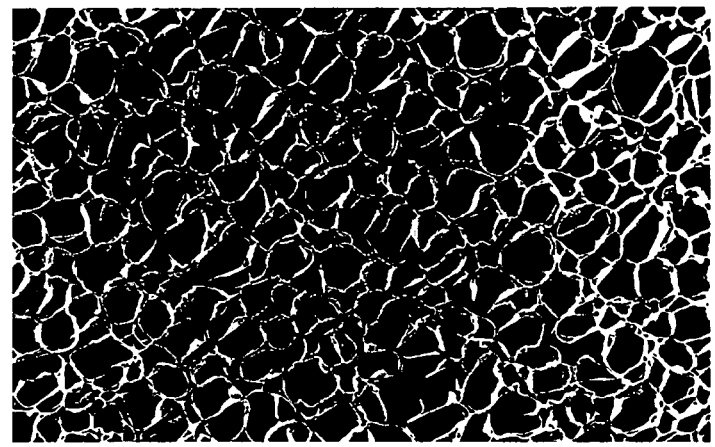
Figure 8:
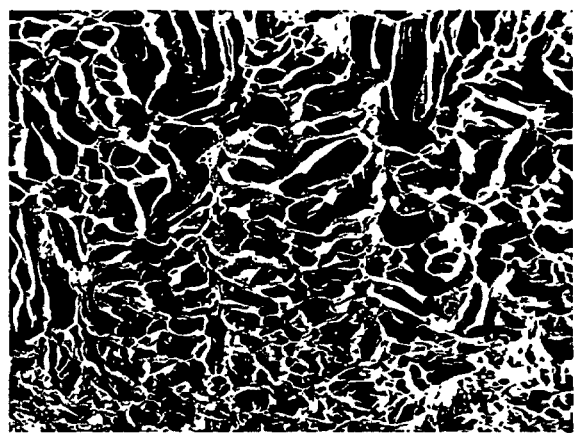
Figure 9:
Figure 10:

Referring now to the figures, those of FIGS. 1-10 illustrate Scanning Electron Microscope (SEM) images of four different vascular grafts made from four different species of polymer using the gel-enhanced phase separation technique. In particular, FIGS. 1, 4 and 7 are SEM images, taken at 250×, 240× and 260× magnification, respectively, showing the external graft surface using a siloxane polyurethane polymer, a carbonate polyurethane polymer, and a resorbable lactic acid polymer. These polymers are exemplary, and not limiting, it is recognized that these and other polymers alone or in combination (e.g., a polycarbonate-siloxane polyurethane polymer, etc.) may be capable of being constructed into a device in accordance with the teachings of the present invention. The external surfaces have a high overall porosity. In contrast, the luminal sides of the grafts have a smooth, low pore surface to minimize flow disturbances. See, for example, FIGS. 3, 6 and 9, which are SEM images at 250× magnification of the luminal surface of vascular grafts made from the siloxane polyurethane polymer, the carbonate polyurethane polymer, and the resorbable lactic acid polymer, respectively. FIGS. 2, 5 and 8 are the corresponding SEM images through the cross-section of the above-mentioned polyurethane and lactic acid polymer grafts, but taken at magnifications of 250×, 260× and 150×, respectively. FIG. 10 is a 250× magnification SEM image of a cross-section of a vascular graft made from a non-resorbable Teflon® polymer. This area of the prosthesis provides multiple chambers capable of carrying other substances and provides a high surface area for cellular attachment while resisting flow through the graft.

Figure 11:
FIG. 11 is an optical photograph showing a pattern of tissue invasion into the porosity of the graft.

The speed and extent of peripheral tissue ingrowth determines the long-term compliance of the graft. FIG. 11 is a 100× magnification optical photomicrograph showing fronds of tissue growing into the pores of a porous prosthesis and expanding to form an intercommunicating tissue network. The type, size and density of the pores of the vascular graft of the present invention not only affects the speed and extent of peripheral tissue ingrowth, but also influences the development and stability of an intimal endothelial layer. Upon implantation, the graft surface in contact with the host tissue bed typically is of a higher overall pore density so that tissue can quickly grow into the prosthesis and secure it (compare, for example, FIG. 7 with FIG. 8). In contrast, the luminal surface of the graft usually has a smooth, low pore density surface in contact with blood to minimize flow disturbances. Not entirely without intercommunication, the luminal surface of the conduit does present enough porosity so that the new cellular lining can be anchored to the tissue that has grown into the device (compare, for example, FIG. 9 with FIG. 8). The average pore size ranges from about 10 to about 300 microns in diameter, preferably about 30 to about 75 microns in diameter.

Present commercially available vascular prostheses fail to form a complete endothelial lining. At best they have an anastomotic pannus formation that rarely achieves 2 cm in length. To achieve long-term patency, a prosthesis probably will require complete endothelialization, and such can only be supported if there is full micro-vessel invasion from the surrounding connective tissue into the interstices of the prosthetic device, nourishing the neointima. Accordingly, in the second aspect of the present invention, where a secondary bioresorbable "microstructure" material is incorporated into the interstices of the polyurethane graft "macrostructure", such investment of the secondary bioresorbable material can encourage the formation of the complete endothelial layer, e.g., by allowing for ingrowth of collateral circulation to nourish the cells within the prosthesis.

Materials such as collagen gels have been utilized for years to avoid pre-clotting of vascular grafts and to improve biocompatibility of the implant. Due to the high solubility of these materials, their benefits are short lived. Within a matter of hours these gels are stripped out leaving the prosthesis nude. Several hours may provide sufficient time to avoid pre-clotting, but is not adequate to aid in tissue integration. In response to the foreign material the body forms a dense tissue capsule over the external surface of the graft. This capsule prevents infiltration of micro vessels through the prosthesis necessary to stabilize an endothelial layer on the luminal surface.

In contrast, and in a particularly preferred embodiment of the present invention, the pore structure of the present prosthesis accommodates and protects the collagen gel (refer again to FIG. 12). Additionally, once incorporated, the gel may be lyophilized and cross-linked. Preferably, the cross-linking will be accomplished by a di-hydrothermal technique that does not require the use of toxic chemicals. The pore structure and cross-linking should allow the gel to remain within the pore structure of the graft for several days, instead of hours. This additional time should be sufficient to encourage cells to enter the device and attach to each polymer partition making up the graft, forming a living tissue barrier between the material of the graft and host cells and body fluids. Micro vessels are now free to grow from the external tissue bed, between the individually encapsulated polymer partitions, where they can stabilize a luminal endothelial layer. During that time between implantation and cellular invasion, the microstructure will provide increased resistance to fluid leakage and influence the biomechanical properties. In this way, a more compliant macrostructure can be implanted which possesses characteristics that can be tailored to those of the host vessel by the physical properties of the microstructure. Specifically, the porous polymeric material is very compliant, and if the porous polymeric material ends up being more compliant than the tissue to which it is to be grafted, the secondary bioabsorbable material can reduce the overall compliance of the prosthesis to approximately that of the host tissue. Over time, host cells, which dictate the overall compliance of the graft, replace the microstructure.

Additionally, the di-hydrothermally cross-linked microstructure provides a larger window of time for utilization of biologically active agents than would exist for the gel alone. Growth factors can be retained within the boundaries of the prosthesis for an extended period of time where they can influence cells entering the device. The effective lifetime of anti-coagulants can be extended, providing additional protection until endothelialization occurs.

A different approach to promotion of capillary endothelialization through the walls of the vascular graft is disclosed in U.S. Pat. No. 5,744,515 to Clapper. Specifically, the graft is sufficiently porous to allow capillary endothelialization, and features near at least the exterior wall of the graft a coating of tenaciously bound adhesion molecules that promote the ingrowth of endothelial cells into the porosity of the graft material. The adhesion molecules are typically large proteins, carbohydrates or glycoproteins, and include laminin, fibronectin, collagen, vitronectin and tenascin. Clapper states that the adhesion molecules are supplied in a quantity or density of at most only about 1-10 monolayers on the surface of the graft, and specifically on the pore surface. Thus, unlike the present secondary bioabsorbable materials, the adhesion molecules of Clapper seemingly would have a negligible effect on, for example, tailoring the mechanical characteristics of the graft, e.g., mechanical compliance.

Figure 13:
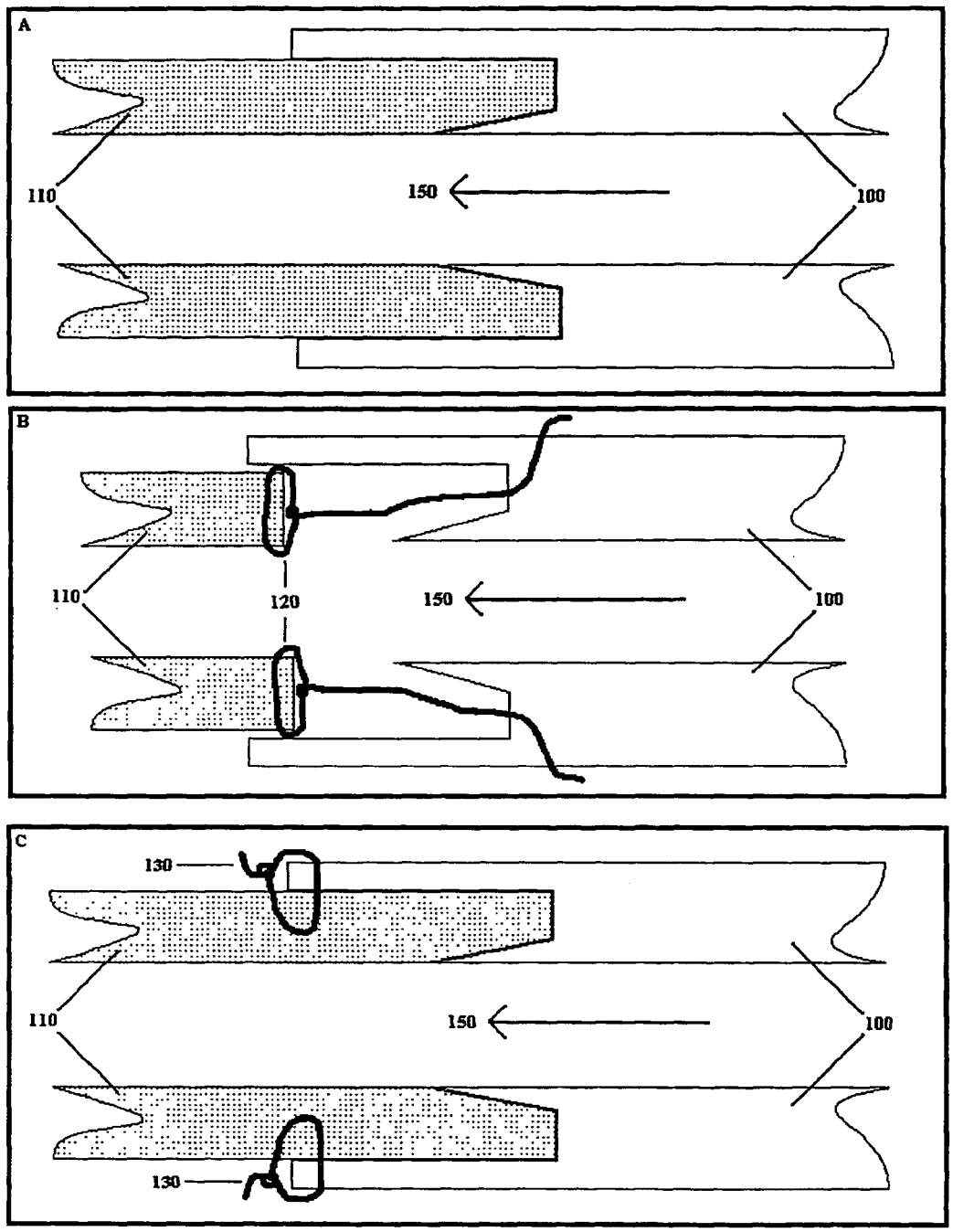
FIGS. 13a-13c show a possible embodiment of the present invention allowing for improved suturing.
Figure 14:
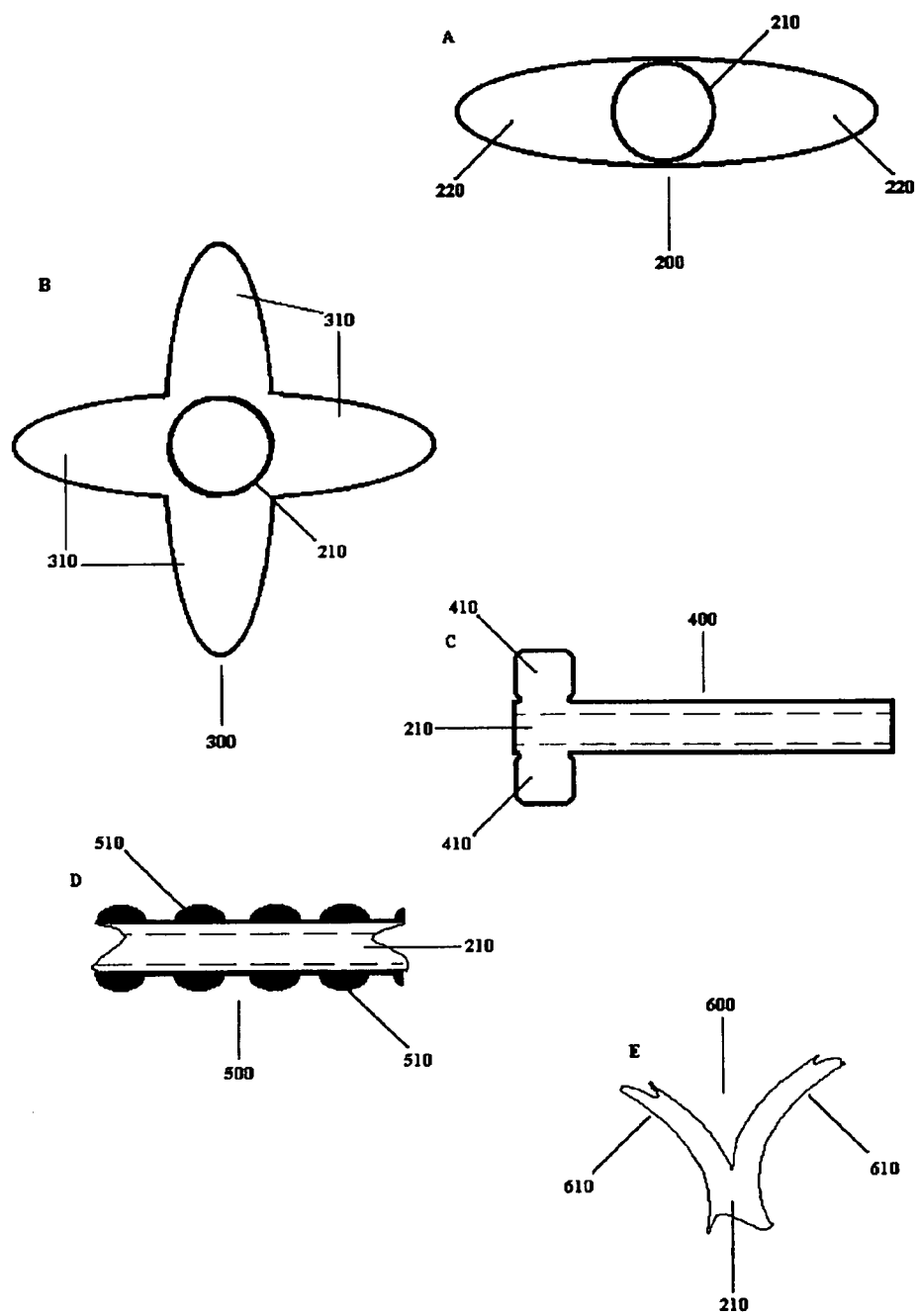
FIGS. 14a-14d show various embodiments of the present invention made possible by the gel enhanced phase separation technique.
FIG. 14e depicts a "Y" graft 600 used to split the blood flow from the central axis 210 into a plurality of graft bifurcations 610.

Again, one of the primary application areas envisioned for the present invention includes a prosthesis for use in vascular reconstructive surgery of mammals, including humans and other primates. The prosthesis may be used to repair, replace or augment a diseased or defective vein or artery of the body. A prosthesis in accordance with the present invention may beneficially be shaped as a vascular graft, and may, for example, have at least one end or section be shaped for optimal fluid flow. FIG. 13, for example, shows non-limiting embodiments of the present invention allowing for improved suturing. Specifically, FIG. 13a shows how the host vessel 110, situated into the graft material 100, provides less resistance to flow through the lumen. (Like numbers refer to like items, and are therefore omitted for brevity.) FIGS. 13b and 13c show how sutures can be placed so that they do not encroach upon the lumen, thus minimizing flow disturbances. A longitudinal suturing method 120 is shown, and compared to a transverse method 130. FIG. 14 shows a representative, but non-limiting selection of various physical or structural embodiments of the present invention made possible by use of the gel-enhanced phase separation technique. For example, FIG. 14a is an end-on view of a vascular graft showing that the present vascular graft may be provided with a pair of flaps 220, extending from the central axis 210 to prevent rolling of the graft 200 once implanted. The vascular graft 300 of FIG. 14b provides additional support when compared to FIG. 14a, namely, by providing two pairs of flaps 310. FIG. 14c illustrates a graft 400 with wings 410 to facilitate suturing. FIG. 14d is a view of a longitudinal section through a graft 500 showing reinforcement rings 510 around the circumference of the graft. FIG. 14e depicts a "Y" graft 600 used to split the blood flow from the central axis 210 into a plurality of graft bifurcations 610.

The "Y" graft, or branched geometry is particularly useful to the vascular graft embodiment, as well as others, and this and other synthetic grafts may be attached by a port, connector or anastomosis, to an artery, vein, or other tubular or hollow body organ to effect a shunt, bypass, or to create other access to same. Additionally, a graft or other device produced with this invention may comprise a plurality of branches, with each branch having a length or diameter that may vary independently from the other branches. As an example, the inlet or proximal branch may be large, and attached to the large section of aorta, while distal sections may be significantly smaller, and of different lengths, to facilitate attachment to smaller coronary arteries.

The large proximal section could allow adequate blood flow through a single attachment to the aorta, thereby decrease possibility of leakage at various proximal anastomoses, while decreasing the procedural time. Likewise, diametric and length matches, or closer matches, will allow faster and easier connections; since the surgeon can trim the graft section to the appropriate length, and the surgeon will not have to rework the graft material to allow the larger natural vein to connect with the smaller coronary artery, thereby further decreasing procedure time.

This process will allow the graft to be of decreasing diameter with increasing length, thereby approximating the anatomy of the coronary artery system. This allows the surgeon to trim the graft to any length, while maintaining a constant graft-vein diameter ratio, thereby allowing in situ customization of the graft length without incurring turbulent flow due to diameter mismatch.

In addition to facilitating the procedure, by reducing the duration of the surgical procedure and attachment complexity thereof, the diameter tailoring of this embodiment will allow the maintenance of a constant flow velocity, while the volume decreases (following the branches, each of which reduce the flow). This constant velocity is important to keeping bloodborne material in the mix; that is, plaque deposits may be deposited on the arterial wall or bifurcation junctions (e.g., the ostium) in the coronary system, in natural as well as in the synthetic graft.

The tailorable properties of material manufactured by the processes of this present invention allow for the manufacture of grafts and other vascular prostheses that may demonstrate compliance, flexibilities and expansion, under normal or elevated blood pressures, similar to that of natural arteries. This constraint-matching avoids problems associated with existing grafts, that is, these grafts and prostheses readily expand during the systolic pulsing. Grafts or harvested veins that do not expand can cause spikes in blood pressure, and may cause or exacerbate existing problems, including or due to high blood pressures.

A device manufactured by the process of this present invention may be useful for various surgical procedures, including delivery and implantation within the living being laparoscopically, in order to allow implantation with minimal exposure for infections and further allowing a faster recovery period.

The unique characteristics of the many polymer species available, both now as well as those anticipated in the future, make it impractical to provide a comprehensive list of gelling agents. To address this problem, below is provided an example of a step-by-step process for the identification of useful dissolving solvents and gelling agents for a single polymer species, as well as how the solvents/agents may be removed to provide the porous, solid polymer material. This process example provides guidance in how to utilize the information provided in this disclosure; however it is recognized that alternate selection methods and/or criteria are known to those skilled in the art.

EXAMPLE I

This Example demonstrates the production of a porous polymeric material using the gel enhanced phase separation technique of the instant invention.

A siloxane-based macrodiol, aromatic polyurethane, supplied by Aortech Biomaterials, was selected for this example.

The manufacturer identified dimethyl acetimide, n-methyl pyrrolidinone, and tetrahydrofuran as (dissolving) solvents for the polymer.

A 0.25-gram sample of polymer was placed into the bottom of 20 small bottles. Five milliliters of 20 common laboratory solvents, including the three listed by the manufacturer, was added to the bottles, one solvent to each bottle. The bottles were left for 48 hours at room temperature after which they were observed visually to identify those solvents that dissolved or resulted in swelling of the polymer. Twelve solvents were identified and are listed below in Table II along with freezing point ("F.P.", also known as melt point), boiling point ("B.P."), vapor pressure ("V.P."), and solvent group (S.G.) information. (Other properties that can aid in the selection of first solvent and gelling agent include, but are not limited to, density, molecular weight, refractive index, dielectric constant, polarity index, viscosity, surface tension, solubility in water, solubility in alcohol(s), residue, and purity.)

TABLE II

| Vial # | Contents | F.P. | B.P. | V.P. (torr) | S.G. | Result |
|---|---|---|---|---|---|---|
| 2 | acetone | −94.7 | 56.3 | 184.5 @ 20 C. | 6 | swell |
| 5 | chloroform | −63.6 | 61.2 | 158.4 @ 20 C. | 8 | swell |
| 7 | p-dioxane | 11.8 | 101.3 | 29.0 @ 20 C. | 6 | swell |
| 11 | methylene chloride | −95.1 | 39.8 | 436.0 @ 25 C. | 5 | swell |
| 12 | n,n-dimethyl acetimide | −20.0 | 166.1 | 1.3 @ 25 C. | 3 | dissolve |
| 13 | dimethyl sulfoxide | 18.5 | 189.0 | 0.6 @ 25 C. | 3 | swell |
| 14 | 1-methyl-2-pyrrolidone | −24.4 | 202.0 | 4.0 @ 60 C. | 3 | dissolve |
| 15 | Tetrahydrofuran | −108.5 | 66.0 | 142.0 @ 20 C. | 3 | dissolve |
| 16 | toluene | −95.0 | 110.6 | 28.5 @ 20 C. | 7 | swell |
| 17 | m-xylene | −47.7 | 139.3 | 6.0 @ 20 C. | 7 | swell |
| 18 | o-xylene | −25.2 | 144.4 | 6.6 @ 25 C. | 7 | swell |
| 20 | methyl-ethyl-ketone | −86.7 | 79.6 | 90.6 @ 20 C. | 6 | swell |

From the table, Tetrahydrofuran (THF) was selected as the polymer dissolving solvent due to its low freeze point, low boiling point and high vapor pressure. One can see that, for this particular polymer, solvent group #3 is particularly preferred as the dissolving solvent, and that solvent group #6 and group #7 are particularly preferred as the gelling agent. The chart also shows that certain solvents from solvent group #5 and group #8 also gave a positive result, e.g., swelling, but these liquids were in the minority; the majority of liquids from these groups neither dissolved nor swelled the polyurethane. Accordingly, this information can be used to prioritize a search for other suitable liquids.

Five milliliters of a 12.5% solution of polymer and THF was placed into each of 9 small flasks with a magnetic stir bar at the bottom. Twenty milliliters of one of each of the 9 liquids identified as gelling agents was added to each flask with rapid stirring. After 2 minutes, stirring was stopped and the solutions were allowed to sit for 13 minutes. As expected, none of the additions resulted in precipitation of the polymer. As a control, an additional flask of polymer/THF solution was set up and 20 ml of ethanol (e.g., a known failed solvent) was added with rapid stirring. A white precipitate immediately formed. After stirring was stopped the polymer precipitate drifted to the bottom of the flask.

All 9 flasks showed signs of thickening even though the polymer to solvent concentration fell from 12.5% to 2.5%. (The control flask solvents (20 ml ethanol 5-ml THF/Polymer) became less viscous as the polymer fell out of solution.) Other parameters being kept equal, the viscosity of the resulting solution or mixture, upon adding the gelling agent, increases with increasing concentration of polymer and also with the initial additions of gelling agent. The viscosity also depends on the identity of the gelling solvent, and can range from a slight thickening to the formation of a gelatinous solid. At the concentrations listed, p-dioxane, dimethyl sulfoxide, and o-xylene produced the greatest thickening.

Utilizing the information provided in the chart, the following methods were used to remove the solvent and gelling agent:

Sample A

Recognizing that p-dioxane has a freeze point, boiling point and vapor pressure suitable for freeze-drying; the Vial 7 gel was scooped onto a Teflon plate, spread out and frozen. The frozen gel (−15 C) was then placed into a freeze-dryer for 12 hours. The THF, having such a low boiling point and high vapor pressure most likely does not freeze and thus is removed from the system first. Upon subsequently removing the p-dioxane, a white porous sheet was produced with a non-fibrous porosity greater than 90%.

Sample B

Recognizing that dimethyl sulfoxide has a boiling point and vapor pressure non-optimal for freeze-drying, the Vial 13 gel is instead poured onto a Teflon tray, frozen at −15 C and then submerged into a non-solvent (ethanol) at −10 C for 12 hours to leach out the first solvent and gelling agent. (Had the gel been thick enough to form a stable gelatinous mass, freezing and the use of chilled alcohol would not be required.) The sheet was then removed from the alcohol and soaked in distilled water 12 hours, after which it is dried and placed into a desiccator. The sheet formed was relatively stiff and had a non-fibrous porosity of greater that 75%.

Sample C

Comparing the boiling point and vapor pressure of o-xylene and THF, the skilled artisan can see that it would be possible to heat the gel and selectively remove the THF solvent and leave the o-xylene gelling agent behind. Accordingly, the Vial 18 gel was poured into a Teflon dish and slowly heated from 21 C to 66 C over a 3-hour period. This increased the viscosity to that of a non-flowing gel without mechanical competence. The dish was then lowered into a 21C-ethanol bath for 12 hours to remove the o-xylene and any residual THF. A light tan sheet was produced with a non-fibrous porosity greater than 40%.

COMPARATIVE EXAMPLE I

Instead of first dissolving the polyurethane in the THF, an attempt was made to dissolve the polyurethane in a solution of THF and gelling agent provided in the same ratio as in the Example. The polyurethane did not dissolve.

Thus, the Example and Comparative Example show: (1) that in the polyurethane/THF system, ethanol is a failed solvent that causes polyurethane to precipitate; (2) that the polymer preferably is dissolved before being exposed to the gelling agent; (3) that different gelling agents affect the solution viscosity to a different degree; and (4) that there are different ways to precipitate the porous polymer from solution, and that the preferred technique may depend upon the properties of the dissolving solvent and gelling agent.

EXAMPLE II

This Example demonstrates that the role of a particular liquid, e.g., dissolving agent ("solvent") or gelling agent, depends to some degree on the nature of the polymer being acted upon.

Table III below show the results of screening tests of various liquids on two candidate polymers. Again, in these screening tests, individual liquids were contacted with solid polymer and observed for effects.

Table III

| | Liquid | Silioxane Polyurethane | Carbonate Polyurethane |
|---|---|---|---|
| 1 | Acetic acid | Non-solvent | Non-Solvent |
| 2 | Acetone | Swelling solvent | Swelling solvent |
| 3 | Acetonitrile | Non-solvent | Non-solvent |
| 4 | Tert-butyl alcohol | Non-solvent | Non-solvent |
| 5 | Chloroform | Swelling solvent | Swelling solvent |
| 6 | Cyclohexane | Non-solvent | Non-solvent |
| 7 | p-dioxane | Swelling solvent | Swelling solvent |

-continued

| | Liquid | Silioxane Polyurethane | Carbonate Polyurethane |
|---|---|---|---|
| 8 | Ethanol | Non-solvent | Non-solvent |
| 9 | Isopropanol | Non-solvent | Non-solvent |
| 10 | Methanol | Non-solvent | Non-solvent |
| 11 | Methylene chloride | Swelling solvent | Swelling solvent |
| 12 | N,n-dimethyl acetimide | Solvent | Solvent |
| 13 | Dimethyl sulfoxide | Swelling solvent | Swelling solvent |
| 14 | 1-methyl-2 pyrrolidone | Solvent | Swelling solvent |
| 15 | Tetrahydrofuran | Solvent | Solvent |
| 16 | Toluene | Swelling solvent | Non-solvent |
| 17 | m-xylene | Swelling solvent | Non-solvent |
| 18 | o-xylene | Swelling solvent | Non-solvent |
| 19 | 1-propanol | Non-solvent | Non-solvent |
| 20 | Methyl-ethyl-ketone | Swelling solvent | Swelling solvent |
| 21 | Benzene | Swelling solvent | Swelling solvent |

Note that both polymers are of the polyurethane genus, and are simply different species of polyurethane; that is, they have different copolymers alloyed in them.

In most cases, the liquid has the same effect in each case, and thus, would perform the same role. On the other hand, the Table III shows a number of instances in which the liquid does not perform the same role. Specifically, 1-methyl-2 pyrolidine will dissolve a siloxane based polyurethane, but will only swell up a carbonate based polyurethane. Similarly, toluene functions as a swelling solvent for the siloxane based polyurethane, but is a non-solvent for the carbonate based polyurethane, and would cause precipitation of carbonate polyurethane solution into two distinct phases.

In addition to polymer species, the physical and chemical properties of a single polymer species (e.g. molecular weight, melt point, freeze point, glass transition temperature, polydispersity, etc.) result in variations in a candidate solvent's effectiveness. For example, a single solvent may function as a dissolving solvent for a low molecular weight polymer, as a swelling solvent for a slightly higher molecular weight polymer and as a non-solvent (failed solvent) for a high molecular weight polymer. In other words, the ability of any given liquid to dissolve a particular polymer species can be dependent upon, among other properties, the molecular weight of the polymer molecules. In general, the higher the molecular weight of a given polymer, the more difficult it is to dissolve it with a given solvent. Thus, it is important to follow the teaching of the above examples in identifying appropriate dissolving solvents, swelling solvents, and non-solvents.

EXAMPLE III

This Example demonstrates the dual-tiered drug delivery technique of the instant invention.

A polycarbonate-siloxane macrostructure may be prepared in accordance with the macrostructure process described above, where the polymer may be solvated in a suitable first solvent (i.e., one that dissolves the polymer fully), and a suitable gelling solvent may be added to cause the gelation of the polymer solution. The gel is then shaped and the solvents removed as described above, resulting in a porous polymer material, e.g., a macrostructure. A microstructure is created within the chambers of the macrostructure, through the incorporation of a soluble collagen and hyaluronan, which is preferably lyophilized within the macrostructure. In order to create a dual-tiered drug delivery device, an amount of heparin is embedded in the microstructure for early elution, preferably by being added to the polymer of the microstructure before incorporation into the macrostructure. A second biologically active agent, herein heparin and sirolimus, is incorporated within the polymer of the macrostructure, preferably by adding the biologically active agent into the polymer/solvent solution, before gelation by the gelling agent.

Upon implantation, the microstructure delivers the heparin to the system of the living being, preventing the formation of local blood clots while cells incorporate and grow on the implant. Subsequently, the macrostructure releases the heparin and sirolimus, preventing the excessive proliferation of cells, and eliminating the occurrence of hyperplasia.

Having taught the reasoning process that is used in choosing appropriate first and second solvents for a given polymer, appropriate techniques for their removal once a desired shape has been fabricated, and described the construction of a dual-tiered drug delivery device, an artisan of ordinary skill can readily identify without undue experimentation other polymer/first solvent/second solvent systems that can be processed similarly to what has been described herein to produce porous polymeric bodies. Accordingly, the artisan of ordinary skill will readily appreciate that numerous modifications may be made to what has been described above without departing from the claimed invention, the scope of which is set forth in the claims to follow.

Having thus described the invention, what is claimed is:

1. A process for making a porous polymeric material, comprising the steps of:
   (a) providing a polymer consisting essentially of polyurethane comprising a siloxane moiety or a carbonate moiety;
   (b) identifying a liquid swelling agent that does not dissolve the polymer in solid form, but instead merely swells the solid polymer, said liquid swelling agent being selected from the group consisting of p-dioxane and dimethyl sulfoxide;
   (c) providing at least sufficient tetrahydrofuran to said polymer as to dissolve the polymer in the tetrahydrofuran to form a solution;
   (d) adding a quantity of the liquid swelling agent to the solution, whereupon the entire volume of solution begins to increase its viscosity without forming a separation of solid and liquid phases;
   (e) continuing to add the liquid swelling agent to the solution until the entire volume of solution transforms to gel, the gelation being without visible separation of a solid phase and a liquid phase;
   (f) shape-forming the gel; and (g) removing the tetrahydrofuran and liquid swelling agent from the gel.

2. The process of claim 1, wherein, at least at some point during processing, at least one biologically active agent is mixed with the polymer and first solvent prior to addition of the swelling agent.

3. The process of claim 1, wherein the gel is placed in contact with a separate body, after which the first solvent and swelling agent are removed, leaving the porous polymer mechanically bound to the body.

4. The process of claim 1, wherein said polymer comprises said siloxane moieties, and further wherein said polyurethane comprises an aromatic polyurethane.

5. The process of claim 1, wherein said polymer comprises said siloxane moieties, and further wherein said polyurethane comprises a macrodiol aromatic polyurethane.

6. The process of claim 1, wherein said solution comprises about 12.5 percent of said polymer in said tetrahydrofuran.

* * * * *